United States Patent
Van Damme et al.

(10) Patent No.: US 9,433,601 B2
(45) Date of Patent: *Sep. 6, 2016

(54) CHEWING GUM COMPOSITIONS COMPRISING CANNABINOIDS

(71) Applicant: Stichting Sanammad, Nijmegen (NL)

(72) Inventors: Philippus Anne Van Damme, Nijmegen (NL); George Evgeniyevich Anastassov, New York, NY (US)

(73) Assignee: Stichting Sanammad, Nijmegen (NL)

(*) Notice: Subject to any disclaimer, the term of this patent is extended or adjusted under 35 U.S.C. 154(b) by 0 days.

This patent is subject to a terminal disclaimer.

(21) Appl. No.: 14/684,109

(22) Filed: Apr. 10, 2015

(65) Prior Publication Data

US 2015/0209322 A1 Jul. 30, 2015

Related U.S. Application Data

(63) Continuation of application No. 12/934,633, filed as application No. PCT/NL2009/050149 on Mar. 26, 2009, now Pat. No. 9,023,322.

(60) Provisional application No. 61/039,451, filed on Mar. 26, 2008.

(51) Int. Cl.
| | |
|---|---|
| *A61K 31/352* | (2006.01) |
| *A61K 9/68* | (2006.01) |
| *B65D 75/36* | (2006.01) |
| *B65D 85/00* | (2006.01) |

(52) U.S. Cl.
CPC ......... *A61K 31/352* (2013.01); *A61K 9/0058* (2013.01); *B65D 75/36* (2013.01); *B65D 85/70* (2013.01)

(58) Field of Classification Search
None
See application file for complete search history.

(56) References Cited

U.S. PATENT DOCUMENTS

| | | | |
|---|---|---|---|
| 4,187,320 | A | 2/1980 | Koch et al. |
| 4,988,683 | A | 1/1991 | Corbiere |
| 5,470,566 | A | 11/1995 | Lutzen |
| 5,487,902 | A | 1/1996 | Andersen et al. |
| 6,986,907 | B2 | 1/2006 | Phillips et al. |
| 2002/0160043 | A1 | 10/2002 | Coleman |
| 2004/0028772 | A1 | 2/2004 | Andersen |
| 2005/0090468 | A1 | 4/2005 | Jarvinen et al. |
| 2006/0045934 | A1 | 3/2006 | Kabse et al. |
| 2006/0115433 | A1 | 6/2006 | Andersen et al. |
| 2006/0257463 | A1 | 11/2006 | Elsohly et al. |
| 2011/0097283 | A1 | 4/2011 | Van Damme et al. |

FOREIGN PATENT DOCUMENTS

| | | |
|---|---|---|
| CA | 2664315 | 3/2008 |
| EP | 1 651 059 | 5/2006 |
| GB | 2 377 633 A | 1/2003 |
| GB | 2 381 194 A | 4/2003 |
| GB | 2 432 312 A | 5/2007 |
| GB | 2 414 933 B | 7/2009 |
| WO | WO-99/08659 A1 | 2/1999 |
| WO | WO-03/101357 A1 | 12/2003 |
| WO | WO-2005/011397 | 2/2005 |
| WO | WO-2005/023226 A1 | 3/2005 |
| WO | WO-2006/010939 | 2/2006 |
| WO | WO-2008/011177 A2 | 1/2008 |
| WO | WO-2008/033024 A2 | 3/2008 |
| WO | WO 2008/098195 A2 | 8/2008 |
| WO | WO-2009/120080 A1 | 10/2009 |

OTHER PUBLICATIONS

Birgitte Hyrup et al., The MediChew Technology platform.
First Examination Report in IN Appln No. 7336/DELNP/2010 dated Nov. 20, 2014.
Gennaro, et al. "Pharmaceutical Sciences", Remington's 17th (1985). Mack Publishing Company.
Imfeld "Chewing Gum—Facts and Fiction: A Review of Gum-chewing and Oral Health", Crit Rev Oral Biol Med (1999), vol. 10., No. 3, pp. 405-419.
International Search Report mailed Jul. 10, 2009 in PCT/NL2009/050149, 3 pages.
Jacobsen, et al. "Medicated Chewing Gum—Pros and Conds", Am J. Drug Deliv. (2004), vol. 2, No. 2, pp. 75-88.
Kalasz, et al. "Drug Excipients", Current Medicinal Chemistry (2006), vol. 13, pp. 2535-2563.
Package information for nicotine gum sold by Topcare; downloaded Apr. 2, 2012.
Package insert for topcare nicotine gum downloaded Apr. 2, 2012 from the site: http://dailymed.nlm.nih.gov/dailymed/druginfo.cfm.
Patent information for Cesamet (generic Nabilone) downloaded Apr. 3, 2012 from the site http://www.cesamet.com.
Zhang, et al. "Oral Mucosal Drug Delivery Clinical Pharmacokinetics and Therapeutic Applications". Clin Pharmacokinet (2002), vol. 41, No. 9, pp. 661-680.

*Primary Examiner* — Frederick Krass
*Assistant Examiner* — Michael P Cohen
(74) *Attorney, Agent, or Firm* — Foley & Lardner LLP; Sunit Talapatra

(57) ABSTRACT

The present invention relates to a chewing gum composition comprising 0.01 to 15% by weight a cannabinoid or a derivative thereof, based on the total weight of the chewing gum composition, and to chewing gums and blistering packages comprising said chewing gums.

16 Claims, No Drawings

CHEWING GUM COMPOSITIONS COMPRISING CANNABINOIDS

CROSS-REFERENCE TO RELATED APPLICATION(S)

This application is a continuation of U.S. patent application Ser. No. 12/934,633, filed Dec. 14, 2010 as the National Phase of International Patent Application No. PCT/NL2009/050149, filed Mar. 26, 2009, which claims the benefit of U.S. Provisional Patent Application No. 61/039,451, filed Mar. 26, 2008. The contents of these applications are herein incorporated by reference in their entirety.

FIELD OF THE INVENTION

1. Field of the Invention

The present invention relates to a chewing gum composition comprising a cannabinoid or a derivative thereof and the use of said chewing gum composition for the treatment or alleviation of pain.

2. Background of the Invention

*Cannabis* has long been used for medicinal purposes and as a recreational drug. The medicinal application is essentially anti-emetic, i.e. that the active components of *cannabis*, i.e. cannabinoids, are effective as a drug against nausea and vomiting which are commonly side-effects of opioid analgesics, anaesthetics, highly active anti-retroviral therapy (HAART for HIV-AIDS) and chemotherapy for cancer. *Cannabis* has also been used for a long period of time as a drug for relieving (chronic neurogenic/neuropathic) pain that is caused by several disorders and surgical operations. Other medical indications include depression, migraine, multiple sclerosis, fibromyalgia, syndromes like Parkinson and Gilles de la Tourette and its use as analgesic, spasmolytic, appetite stimulating, palliative and anti-convulsant medication.

The main constituent of *cannabis* is delta-9-tetrahydrocannabinol (THC) or dronabinol. Its IUPAC nomenclature is (−)-(6aR,10aR)-6,6,9-trimethyl-3-pentyl-6a,7,8,10a-tetrahydro-6H-benzo[c]chromen-1-ol). THC binds to the cannabinoid receptor $CB_1$ (agonist) which is located in brain tissue. Other active components of *cannabis* include cannabidiol (CBD; 2-((1S,6S)-3-methyl-6-(prop-1-en-2-yl)cyclohex-2-enyl)-5-pentylbenzene-1,3-diol) and cannabichromene (CBC). CBD is not binding to the $CB_1$ or the $CB_2$ receptor whereas CBC is believed to have an anti-inflammatory action and would contribute to the pain relieving effect of *cannabis*.

*Cannabis* is usually inhaled by the patient (*cannabis* is often mixed with tobacco for smoking purposes). Smoking has a rapid onset (minutes) and the dosage can be easily controlled by the patient. However, smoking is not always convenient, since it is reported to have an adverse affect on the respiratory system and many patients just dislike smoking. Additionally, smoking of *cannabis* includes burning of the herb which may lead to the formation of harmful side-products like noxious carbon monoxide. Furthermore, the harmful effects of nicotine and tar are well known. Although effective, smoking *cannabis* has many disadvantages.

Another method frequently employed is vaporisation wherein the herb is heated to about 180° C. rather than burned so that harmful side-products are hardly formed. Additionally, the vapour may be cooled or further purified if desired before inhalation. Furthermore, the dosage is easily controlled by the patient since inhalation provides for a rapid onset and a fast delivery into the bloodstream. However, the use of a vaporiser is also not always convenient since it requires a place or spot where the patient can set up and use his or her vaporiser to undergo treatment. In this respect it is also time-consuming.

Oral compositions comprising synthetic THC, e.g. gelatine capsules and tablets, are also known in the art. Marinol® (active component is dronabinol or (−)-(6aR,10aR)-6,6,9-trimethyl-3-pentyl-6a,7,8,10a-tetrahydro-6H-benzo[c]chromen-1-ol) is a soft gelatine capsule a 2.5 mg comprising synthetic THC. A disadvantage of this product is the high price and that it takes about an hour to take full effect and the frequent dosage problems encountered by patients. The bio-availability after oral intake is only approximately 15%. Namisol® (active component is dronabinol) is a sublingual tablet a 1.4 mg THC (ultra pure extract from *cannabis sativa*), which is claimed to have a rapid uptake through the sublingual mucosa. The problem is that the tablet has to be kept under the tongue for the time it takes to dissolve in the saliva.

Cesamet® (active component is nabilone) is a capsule comprising the synthetic cannabinoid nabilone (racemic (6aR,10aR)-1-hydroxy-6,6-dimethyl-3-(2-methyloctan-2-yl)-7,8,10,10a-tetrahydro-6H-benzo[c]chromen-9(6aH)-one). It is said to have fewer undesired side effects than THC.

Sativex® comprises THC and CBD and is commercially available as a buccal mouth spray for multiple sclerosis and for the alleviation of pain. Each spray of Sativex® delivers a fixed dose of 2.7 mg THC and 2.5 mg CBD. It is reported to cause irritation of the oral mucosa (20-25% of the patients) and to have a bad taste because of the high ethanol content.

However, gelatine capsules comprising THC or similar components appear to be less effective than smoking *cannabis* or vaporising *cannabis* and inhaling the vapour formed. Moreover, patients suffering from severe nausea due to chemotherapy complained that these oral formulations were difficult to swallow.

GB 2377633 of GW Pharmaceuticals, incorporated by reference, discloses pharmaceutical compositions comprising cannabinoids having specific ratios of cannabidiol (CBD) to tetrahydrocannabinol (THC). The compositions are clinically useful in the treatment or management of specific diseases or medical conditions.

GB 2381194 of GW Pharmaceuticals, incorporated by reference, discloses pharmaceutical formulations for use in the administration of medicaments, in particular lipophilic medicaments, via mucosal surfaces. Example 9 discloses a formulation for buccal use and sublingual tablets.

GB 2414933 of GW Pharma Ltd., incorporated by reference, discloses the use of a combination of cannabinoids for the treatment of pain, inflammation and/or disease modification in arthritis. The cannabinoids are selected from CBD or cannabidivarin (CBDV) and THC or tetrahydrocannabinovarin (THCV) and are in a predefined ratio by weight of less than or equal to 19:1 of CBD or CBDV to THC or THCV.

GB 2432312 of GW Pharma Ltd., incorporated by reference, discloses the use of a combination of cannabinoids in the treatment of neuropathic pain, in particular peripheral neuropathic pain. A combination of CBD and THC may be used, wherein the ratio of CBD:THC by weight is between 10:1 and 1:10.

There is still a need in the art for a composition comprising a cannabinoid that can be used by a mammal, preferably a human, suffering from pain for the treatment or alleviation of said pain, wherein said composition can be used in a mammal friendly, preferably man-friendly, and socially accepted manner including situations and locations where smoking is legally not allowed or is not convenient or is hampering or irritating other mammals, preferably humans, such as in restaurants, train stations, café's and the like. There is further a need in the art for a composition comprising a cannabinoid or a derivative thereof that can be used as a unit dosage form, in particular a unit dosage form that is easily and safely packed in a suitable carrier, e.g. a blister package so that it can be easily carried by the consumer. There is also a need in the art for compositions comprising a cannabinoid or a derivative thereof that allows for controlled release of the cannabinoid or the derivative thereof. Additionally, there is a need in the art for better dissolving of lipophilic cannabinoids and improving or masking the unpleasant taste of these lipophilic cannabinoids.

SUMMARY OF THE INVENTION

The present invention relates to a chewing gum composition comprising a cannabinoid or a derivative thereof. The present invention further relates to the use of said chewing gum composition for the treatment or alleviation of pain.

DETAILED DESCRIPTION OF THE INVENTION

The verb "to comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one". Additionally, the words "a" and "an" when used in the present document in concert with the word comprising or containing denote "one or more."

The present invention relates in particular to a chewing gum composition comprising a cannabinoid or a derivative thereof that allows for controlled release of the cannabinoid or the derivative thereof thereby providing a sustained and prolonged release of the cannabinoid or the derivative thereof, so that a mammal, preferably a human, consuming the chewing gum composition is free of pain or is alleviated from pain for a prolonged period of time.

According to the present invention, it is preferred that the chewing gum composition comprises 0.01 to 15% by weight of the cannabinoid or the derivative thereof, more preferably 0.01 to 1.0 wt. %, even more preferably 0.05 to 0.125% by weight, yet even more preferably 0.1 to 0.10% by weight, based on the total weight of the composition.

The chewing gum composition comprising the cannabinoid or the derivative thereof further comprises a gum base as is commonly used in chewing gum formulations that are commercially available and accepted by the consumer.

The cannabinoid or the derivative thereof may be comprised by a solid material composed of a cellulose which comprises a well-defined amount of the cannabinoid or the derivative thereof, e.g. in and/or onto voids or pores within the solid material.

Preferably, the chewing gum composition according to the present invention has a high initial release rate of the cannabinoid or the derivative thereof to provide a rapid alleviation of pain. Accordingly, it is preferred that the chewing gum composition according to the present invention releases at least 1% by weight to not more than 30% by weight, based on the total weight content of the cannabinoid or the derivative thereof in the chewing gum composition according to the present invention within five minutes after ingestion. It is also preferred that the onset of the release starts within three minutes after ingestion.

Preferably, the chewing gum composition is non-disintegrating, i.e. it does not disintegrate during chewing, and it does not crumble. It is currently contemplated that use of a particular gum base in combination with a suitable selection of additives has a significant impact on the non-disintegrating properties of chewing gum compositions. Examples of suitable gum bases having suitable properties and leading to non-disintegrating chewing gum compositions are e.g. gum bases that are or comprise, Gum powder PG 11 TA, Gum powder PG 11 TA New, Gum powder PG 5 TA, Gum powder PG 5 TA New and Gum powder PG N12 TA.

The gum base is normally present in the chewing gum composition according to the present invention in an amount of about 25 to about 85% by weight, preferably about 30 to about 80% by weight, more preferably about 40% to about 80% by weight and in particular about 50 to about 80% w/w, based on the total weight of the chewing gum composition.

In preferred embodiments of the chewing gum compositions according to the present invention, the chewing gum composition comprises one or more further ingredients, e.g. fats, waxes, emulsifiers, plasticizers, oils, flavouring agents and the like.

The chewing gum composition according to the present invention may comprise a carrier comprising internal voids. Such voids may at least partially comprise said cannabinoid or derivative thereof. The carrier is preferably essentially insoluble in water or has a very low solubility in water. Thus, it has typically a solubility in water at room temperature (25° C.) of less than 1% w/w. Obviously, the solubility under intra-oral mouth temperature conditions (which is higher than 25° C.) should also be not too high.

Suitable carriers are certain cellulose, such as a microcrystalline cellulose derivatives, e.g. microcrystalline cellulose or carbohydrates including a cellulose derivative, e.g. hemicellulose. The cellulose derivative may be of natural origin, e.g. dextran, agarose, agar, pectin, alginate, xanthan, chitosan, starch. The cellulose derivative may also be of synthetic or semi-synthetic origin.

A particular suitable material having internal voids is a microcrystalline cellulose. Specific examples of a suitable microcrystalline cellulose is microcrystalline cellulose selected from the group consisting of AVICEL® grades PH-100, PH-102, PH-103, PH-105, PH-112, PH-113, PH-200, PH-300, PH-302, VIVACEL® grades 101, 102, 12, 20 and EMOCEL® grades 50M and 90M, and the like, and mixtures thereof.

The chewing gum composition according to the present invention preferably further comprises a component selected from the group of flavouring agents, sweetening agents, buffering agents, antioxidants, pharmaceutically acceptable excipients and mixtures thereof In order to improve the organoleptic properties of the chewing gum composition according to the present invention, the chewing gum composition preferably comprises a flavouring agent, e.g., menthol flavour, *eucalyptus*, mint flavour and/or L-menthol, in an amount of about 0.5 to about 12% by weight, more preferably about 1 to about 10% by weight, even more preferably about 1.5 to about 9% by weight, yet even more preferably about 2 to about 8% by weight, based on the total weight of the chewing gum composition.

In order to increase the gustatory properties of the chewing gum composition according to the present invention, the chewing gum composition preferably comprises a pharmaceutically acceptable sweetener, e.g. sugar alcohols including xylitol, sorbitol and/or isomalt, artificial sweeteners such as e.g. aspartame, sucralose, acesulfame potassium or saccharin. The amount of the pharmaceutically acceptable sweetener is normally preferably at least about 0.05% by weight, more preferably about 0.075 to about 5% by weight, even more preferably about 5 to about 35% by weight, yet even more preferably about 10 to about 35% by weight, even yet more preferably about 15 to about 35% by weight and in particular about 20 to about 30% by weight, based on the total weight of the chewing gum composition. It is highly preferred that the pharmaceutically acceptable sweetener is non-cariogenic as well as non-carcinogenic.

The chewing gum composition according to the present invention preferably comprises a buffering agent. Suitable buffering agents are typically those selected from the group consisting of acetates, glycinates, phosphates, glycerophosphates, citrates such as citrates of alkaline metals, carbonates, hydrogen carbonates, and borates, and mixtures thereof. The chewing gum composition preferably comprises a buffering agent in an amount of about 0.5 to about 5% by weight, more preferably about 0.75% to about 4% by weight, even more preferably about 0.75 to about 3% by weight, yet even more preferably about 1 to about 2% by weight, based on the total weight of the chewing gum composition.

The chewing gum composition according to the present invention preferably further comprises an anti-oxidant, e.g., ascorbyl palmitate and sodium ascorbate, in an amount of about 0.05 to about 0.3% by weight, more preferably about 0.1 to about 0.25% by weight, yet even more preferably about 0.15 to about 0.2% by weight, based on the total weight of the chewing gum composition.

The pharmaceutically acceptable excipients used in the chewing composition according to the present invention are preferably selected from the group of excipients normally used within the pharmaceutical industry for the preparation of tablets, i.e. excipients like fillers, desintegrants, binders, lubricants and the like.

Suitable fillers include celluloses and cellulose derivatives including microcrystalline cellulose, hydroxypropylcellulose and sodium carboxymethylcellulose, lactose, starches including potato starch and maize starch (in the US known as corn starch).

Suitable lubricants include stearates including magnesium stearate, talc and colloidal silica dioxide.

Chewing gums can be made from the chewing composition according to the present invention by conventional methods.

The chewing gum prepared from the chewing gum composition according to the present invention may be coated or uncoated.

The chewing gum prepared from the chewing gum composition according to the present invention may comprise a core coated with one or more layers, wherein the core and/or one or more layers comprise (a part of) the total content of the cannabinoid or the derivative thereof which is present in the chewing gum composition thereby enabling a controlled release profile.

The present invention also relates to a blister package comprising a chewing gum composition according to the present invention.

The chewing gum composition according to the present invention is used for the treatment or alleviation of pain, in particular pain resulting from oral and cranio-maxillofacial surgery and/or disorders and/or chronic pain. However, the chewing gum composition according to the present invention may also be used to treat or prevent conditions associated with or caused by chemotherapy and radiotherapy, including nausea, vomiting and muscle spasms.

EXAMPLES

Example 1

Chewing Gum Preparation

A chewing gum base was used to prepare a chewing gum with containing 10.0 mg of THC. Percentages are in percent by weight.

| Gumbase: | 75.5% | A |
| Xylitol: | 13.6% | A |
| Glycerin: | 4.5% | A |
| Saccharine: | 0.38% | B |
| H2O: | 2.26%: | B |
| Peppermint Aroma oil: | 1.51%: | C |
| Peppermint powder: | 1.51% | A |
| THC: | 0.69%: | C |
| Total: | 100% | |

Phase A: The gum base was heated till 90° C. and Xylitol, glycerin and peppermint powder were added and the whole was stirred till a homogeneous mass of gum Phase B: Saccharine was dissolved in $H_2O$.

Phase C: The peppermint oil was heated till 60-70° C. and the THC was added out of a heated syringe and dissolved in the peppermint aroma oil.

Phase B was added to Phase A and stirred vigorously, directly here after Phase C was added and the whole was stirred vigorously for approx 7 minutes.

The gum base was poured on a plate and cooled down.

Hereafter chewing gums with a mass of about 1.5 g were prepared.

Example 2

Case Studies

A chewing gum was chewed for a time period of 20 minutes and a relaxation of the healthy volunteers was observed.

Abbreviations

CBN: Cannabinol
CBD: Cannabidiol
THCC3: Tetrahydrocannabivarin or tetrahydrocannabinol-C3
THCC4: Tetrahydrocannabinol-C4
DHC: Dihydrocannabinol
THC: Tetrahydrocannabinol
CBC: Cannabichromene Method:

Samples were prepared by putting one gum in a 10.0 ml glass laboratory tube. 5.00 ml ethanol was added and the tube was shaken 3 times with a 5 minute interval. Then 5.00 ml mobile phase (acetonitrile: $H_2O+0.1\%$ formic acid) was added. The tube was shaken and the gum was mashed with a Pasteur pipette. Then the solution was shaken again and the sample was filtered through a 0.2 micrometer filter. This is the impurity solution. An assay solution was prepared by diluting the impurity solution 100 times with mobile phase. The calculated amount of THC is based upon comparison with a reference solution with an exactly known amount of THC. Purities are calculated as peak area/sum of area's*100%. Impurities present in the placebo are not considered and known impurities are corrected with known response factors.

Results

TABLE 1

Absolute amounts in three separately measured chewing gums

|  | CBN (mg) | DHC (mg) | THC (mg) | CBC (mg) | Weight (mg) |
| --- | --- | --- | --- | --- | --- |
| Canchew m1 | 0.01 | 0.02 | 2.19 | 0.01 | 1529.3 |
| Canchew m2 | 0.01 | 0.02 | 2.12 | 0.01 | 1593.0 |
| Canchew m3 | 0.01 | 0.02 | 1.96 | 0.01 | 1515.9 |

TABLE 2

Purity based on total area

|  | CBD | THCC3 | THCC4 | CBN | DHC | THC | CBC | SUM |
| --- | --- | --- | --- | --- | --- | --- | --- | --- |
| THC | 0.32 | 0.16 | 0.14 | 0.27 | 0.57 | 98.18 | 0.36 | 100 |
| Canchew m1 | 0.00 | 0.00 | 0.00 | 0.36 | 0.97 | 98.04 | 0.62 | 100 |
| Canchew m2 | 0.00 | 0.00 | 0.00 | 0.32 | 1.04 | 97.99 | 0.65 | 100 |
| Canchew m3 | 0.00 | 0.00 | 0.00 | 0.40 | 1.17 | 97.71 | 0.73 | 100 |

CONCLUSIONS

During the preparation of the chewing gum only a slight degradation of THC occurs. The main breakdown product is dihydrocannabinol which is an intermediate to cannabinol.

Extraction of THC from the chewing gum is not very efficient with the used method. The measurements show only 2 mg THC in each tablet. This is however not consistent with the added amount of THC. Various minor impurities in the used THC cannot be measured in the gum, this is because these are also ineffectively extracted and therefore in very low concentration in the sample.

None of the known breakdown products of THC can be measured and therefore it is not logical that the THC actually got broken down. For this reasons it should be assumed that the individual gums contain about 10 mg THC a piece. During some tests it was experienced that the matrix which contains the THC is insoluble in most solvents. This makes a good recovery and precise measurement extremely difficult. Pentane dissolved the gum and is known to be a good solvent for cannabinoids. It is therefore recommended to do extractions with an aliphatic hydrocarbon. Down side to this procedure is that these samples cannot be directly injected into a reverse phase HPLC system. Gas chromatography would be a good alternative.

The invention claimed is:

1. A chewing gum composition comprising, based on the total weight of the composition:
   (a) 0.01 to 1% by weight of one or more cannabinoids, provided within internal voids of a solid cellulose carrier;
   (b) 25 to 85% by weight of a gum base comprising at least one buffering agent;
   (c) 10 to 35% by weight of at least one sweetening agent;
   (d) 1 to 10% by weight of at least one flavouring agent; and
   wherein 30% by weight of the cannabinoid is released within 5 minutes after ingestion, based on the total weight content of the cannabinoid in the chewing gum composition, and wherein the release starts within 3 minutes after ingestion.

2. The chewing gum composition according to claim 1, wherein the cannabinoids comprise tetrahydrocannabinol (THC).

3. The chewing gum composition according to claim 1, wherein the buffering agent is selected from the group consisting of acetates, glycinates, phosphates, carbonates, glycerophosphates, citrates, borates, and mixtures thereof.

4. The chewing gum composition according to claim 1, wherein the sweetening agent is selected from the group consisting of xylitol, sorbitol, isomalt, aspartame, sucralose, acesulfame potassium, and saccharin.

5. The chewing gum composition according to claim 1, wherein the flavouring agent is selected from the group consisting of menthol flavor, *eucalyptus*, mint flavor and/or L-menthol.

6. The chewing gum composition according to claim 1, wherein the chewing gum composition comprises an antioxidant.

7. The chewing gum composition according to claim 1, wherein the chewing gum composition comprises a pharmaceutically acceptable excipient selected from the group consisting of fillers, disintegrants, binders, lubricants, and antioxidants.

8. The chewing gum composition according to claim 1, wherein the chewing gum composition is non-disintegrating.

9. The chewing gum composition according to claim 1, wherein the chewing gum comprises natural cannabinoid obtained from *cannabis*.

10. The chewing gum composition according to claim 1, wherein the sweetening agent is a sugar alcohol.

11. The chewing gum composition according to claim 1, wherein the sweetening agent is selected from the group consisting of xylitol, sorbitol and/or isomalt.

12. A blister package comprising a chewing gum composition according to claim 1.

13. A method for treating or alleviating pain a mammal in need thereof, comprising administering to said mammal a chewing gum composition according to claim 1.

14. The method according to claim 13, wherein the pain results from oral and cranio-maxillofacial surgery and/or disorders.

15. The method according to claim 13, wherein the pain is chronic.

16. The chewing gum composition according to claim 1, wherein the cannabinoids comprise THC and cannabidiol (CBD).

* * * * *